United States Patent
Mamayek

(10) Patent No.: US 6,406,433 B1
(45) Date of Patent: Jun. 18, 2002

(54) OFF-APERTURE ELECTRICAL CONNECT TRANSDUCER AND METHODS OF MAKING

(75) Inventor: Don S. Mamayek, Mountain View, CA (US)

(73) Assignee: SCIMED Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/358,495

(22) Filed: Jul. 21, 1999

(51) Int. Cl.$^7$ ................................................ A61B 8/00
(52) U.S. Cl. ......................................... 600/459; 29/25.35
(58) Field of Search ................................ 600/437, 447, 600/459; 310/334–336; 29/25.35

(56) References Cited

U.S. PATENT DOCUMENTS

| | | | |
|---|---|---|---|
| 4,101,795 A | * 7/1978 | Fukumoto et al. | 310/336 |
| 4,217,684 A | * 8/1980 | Brisken et al. | 310/334 |
| 4,348,283 A | 9/1982 | Ash | 210/321.3 |
| 4,672,591 A | * 6/1987 | Breimesser et al. | 367/152 |
| 4,704,774 A | * 11/1987 | Fujii et al. | 29/25.35 |
| 4,794,931 A | 1/1989 | Yock | 128/660.03 |
| 4,861,332 A | 8/1989 | Parisi | 604/22 |
| 4,889,128 A | 12/1989 | Millar | 128/662.06 |
| 5,354,220 A | 10/1994 | Ganguly et al. | 439/675 |
| 5,359,760 A | * 11/1994 | Busse et al. | 29/25.35 |
| 5,402,791 A | * 4/1995 | Saitoh et al. | 600/459 |
| 5,423,220 A | * 6/1995 | Finsterwald et al. | 73/642 |
| 5,511,550 A | * 4/1996 | Finsterwald | 600/459 |
| 5,583,293 A | 12/1996 | Flogel | 73/642 |
| 5,732,706 A | 3/1998 | White et al. | 128/661.01 |
| 5,737,963 A | * 4/1998 | Eckert et al. | 310/338 |
| 5,920,972 A | * 7/1999 | Palczewska et al. | 29/25.35 |

FOREIGN PATENT DOCUMENTS

| | | | |
|---|---|---|---|
| EP | 0112562 A2 | 7/1984 | G10K/11/00 |
| FR | 2325266 | 4/1977 | H04R/1/34 |
| JP | 07322393 | 8/1995 | H04R/17/00 |
| JP | 08307995 | 11/1996 | H04R/17/00 |

* cited by examiner

Primary Examiner—Francis J. Jaworski
(74) Attorney, Agent, or Firm—Townsend and Townsend and Crew, LLP

(57) ABSTRACT

The present invention provides ultrasound transducer packages having off-aperture electrical connections, imaging assemblies employing such packages, and methods of making same. In one embodiment, a transducer package (10) for an imaging catheter includes a transducer element (14) and a matching layer (12) operably attached to the transducer element to create an overhang portion (18) of the matching layer. A lead (20) is operably attached to the overhang portion. This arrangement permits the transmission of signals to, and receipt from, the transducer by establishing an electrical connection with the overhang portion via the lead. In another embodiment, the matching layer comprises a thermoplastic which can be tuned to have a desired acoustic impedance according to methods of the present invention.

26 Claims, 5 Drawing Sheets

OFF-APERTURE ELECTRICAL CONNECT TRANSDUCER AND METHODS OF MAKING

BACKGROUND OF THE INVENTION

The present invention relates generally to ultrasonic imaging catheters, and more particularly, to catheters having improved electrical connections for ultrasonic transducers.

Intravascular imaging of blood vessels and surrounding tissues continues to be of great benefit in a wide range of medical fields. A particularly successful design for an intravascular imaging catheter employs a rotatable imaging assembly containing an ultrasonic transducer, where the assembly is attached to the distal end of a flexible drive cable. The transducer may be rotated within a catheter body or sheath in order to transmit an ultrasonic signal and produce a video image by well-known techniques. The transducer element or elements are connected to electronics, typically maintained outside the patient's body, to produce the video image.

To connect the transducer to the electronics, an electrode or lead typically is physically attached to either the transducer face or to the face of a matching layer which is, in turn, attached to the transducer face. However, such an attachment (e.g., a conductive silver epoxy soldered attachment point) can adversely affect the transmission and receipt of ultrasonic signals by the transducer. In short, the attachment interferes with or blocks at least part of the transmitted and/or reflected signals. This problem is further exacerbated by the fact that such attachments often are made by hand. Attachments made by hand typically vary in both size and location from catheter to catheter. As a result, it can be difficult to predict the amount of interference the attachment will produce for a particular imaging catheter.

Further, when a sound wave generated by a typical transducer impinges on an interface between two different media, such as the interface between the transducer face and the tissue being imaged, part of the incident wave is reflected and part is transmitted. The amount of wave reflected compared to the amount transmitted depends primarily on the relative acoustic impedances of the two media. In general, it is desirable to reduce or minimize the difference in acoustic impedance between the two media to permit a greater amount of the wave energy to transmit through the interface. Some existing catheters attach one or more matching layers to the transducer face which have an acoustic impedance between that of the transducer and that of the tissue being imaged. It is desirable, and a further object of the present invention, to provide a method of tuning the matching layer to have a desired acoustic impedance when coupled to the transducer.

SUMMARY OF THE INVENTION

The present invention provides ultrasound transducer packages having off-aperture electrical connections, imaging assemblies employing such packages, and methods of making same. The transducer packages of the present invention are intended to overcome at least some of the problems of the prior art. For example, the present invention moves the electrode or front lead attachment off-aperture, or off the transducer face. This reduces or eliminates the interference such attachment points may cause to the ultrasound signals transmitted from and/or received by the transducer element. Further, imaging assemblies of the present invention are designed to have matching layers that can be tuned to improve impedance matching. Such assemblies are hence more uniform and predictable, and have improved performance.

In one embodiment, the present invention provides a transducer package for an imaging catheter. The transducer package includes a transducer element and a matching layer operably attached to the transducer element to create an overhang portion of the matching layer. A lead is operably attached to the overhang portion. In this manner, signals can be sent from, and received by, the transducer by establishing an electrical connection with the overhang portion via the lead. Preferably, this lead also is attached to an electrical signal source to send electrical signals to the transducer element for ultrasound imaging. The electrical connection is made with a reduced concern as to the size or precise location of the attachment point because the lead or other electrical connection device is attached to the overhang portion of the matching layer and not to the transducer or to the non-overhanging portion of the matching layer face.

Other exemplary off-aperture connection apparatus and methods are disclosed in U.S. Pat. No. 6,036,647, entitled "PZT Off-Aperture Bonding Technique"; U.S. patent application Ser. No. 09/127,089, entitled "Off-Aperture Electrical Connection for Ultrasonic Transducer"; and U.S. Pat. No. 6,162,178, entitled "Ultrasonic Transducer Off-Aperture Connection", the complete disclosures of which are incorporated herein by reference.

In one aspect, the transducer element has first and second spaced apart surfaces, with the first surface having a first area. The matching layer has third and fourth spaced apart surfaces, with the third surface having a second area. The second area is larger than the first area. The third surface is operably attached to the first surface to provide the overhang portion. In one particular aspect, the third surface completely covers the first surface and produces the overhang portion.

In another aspect, the matching layer and transducer element further include a conductive material so that operably attaching the third surface to the first surface produces an electrically conductive path therebetween. In one aspect, the transducer element is operably attached to the matching layer using an epoxy layer.

In one aspect, the matching layer includes a thermoplastic. In this manner, the thermoplastic can be conformed to the appropriate size and/or thickness in order to facilitate impedance matching between the transducer element and the matching layer, and between the matching layer and the tissue or fluid to be imaged. Alternatively, the matching layer includes an uncatalyzed epoxy, a B-stage epoxy, other modifiable materials, and the like. It will be appreciated by those skilled in the art that the matching layer may comprise additional materials within the scope of the present invention.

In another aspect, the transducer package further includes a second matching layer operably attached to the first matching layer. Preferably, the second matching layer has a different acoustic impedance than the first matching layer. For example, in some instances it is desirable for the second matching layer to have an acoustic impedance that is lower than an impedance of the first matching layer, which is in turn lower than the impedance of the transducer element. Such use of matching layer(s) is particularly desirable since transducer elements typically have a significantly higher impedance than an impedance of the surrounding tissue being imaged.

In still another aspect, the transducer package further includes a backing material operably attached to the transducer element. Backing material preferably is used to reduce or eliminate the effect of ultrasound signals propagating from, or received by, the side of the transducer element contacting the backing material. This, in turn, improves the overall performance of the transducer. In one aspect, the transducer element includes a material selected from a group of materials consisting of piezoceramics, piezocomposites, and piezoplastics.

In one particular embodiment of the present invention, a transducer package for an imaging catheter includes a transducer element and a first matching layer operably attached to the transducer element. The first matching layer includes a thermoplastic, such as a thermoplastic film, a thermoset film whose shape is deformable with heat and/or pressure, and the like. In this manner, the use of a thermoplastic matching layer facilitates the tuning of the matching layer to have desired acoustic impedance properties. Additionally, the use of thermoplastics facilitates the use of a curved matching layer with, for example, a transducer element having a curved surface. For example, in one aspect, the transducer element has a first curved surface and the first matching layer has a second curved surface. The transducer element and first matching layer are operably attached so that the first and second curved surfaces are coupled.

Additional uses of curved matching layer and transducer element surfaces are disclosed in U.S. Pat. No. 6,287,261, entitled "Focused Ultrasound Transducer and Systems", the complete disclosure of which is incorporated herein by reference. Additional tuning methods and advantages are disclosed in U.S. patent application Ser. No. 09/127,694, entitled "Method of Tuning Ultrasonic Transducer Matching Layer" now abandoned, the complete disclosure of which is incorporated herein by reference.

In one aspect of the embodiment, the first matching layer is operably attached to the transducer element to create an overhang portion of the first matching layer. In one particular aspect, the transducer package further includes a lead operably attached to the overhang portion. Alternatively, the transducer package further includes a second matching layer operably attached to the first matching layer, preferably in a manner which creates an overhang portion of the second matching layer. The lead again is operably attached to the overhang portion.

The invention further provides an exemplary imaging assembly, which includes a housing having a distal end, a proximal end and a longitudinal axis. A transducer package is operably attached to the housing distal end. The transducer package includes a transducer element, a matching layer, preferably comprising a thermoplastic, operably attached to the transducer element to create an overhang portion of the matching layer, and a lead operably attached to the overhang portion. Preferably, the imaging assembly further includes a drive cable operably attached to the housing proximal end. In this manner, the drive cable rotates the imaging assembly to rotate the transducer package, for example, during ultrasound imaging.

The present invention further provides exemplary methods of making a transducer package. One particular method includes the step of providing a transducer element having first and second electrodes operably attached to first and second transducer element surfaces, respectively. A matching layer is provided having at least one electrically conductive surface. The transducer element and matching layer conductive surface are coupled together with an adhesive layer to produce an electrically conductive path between the first electrode and the matching layer conductive surface. The coupling step further creates an overhang portion of the matching layer. The method includes attaching a lead to the overhang portion. In one aspect of the method, the adhesive layer includes an electrically non-conductive epoxy layer. Other adhesives may be used within the scope of the present invention, including conductive epoxy or adhesive layers.

In one particular aspect, the matching layer includes a thermoplastic. The coupling step includes compressing the matching layer and transducer element together using a desired pressure and a desired temperature. The method includes reducing the temperature after the matching layer and transducer element have been compressed into a desired shape and/or thickness, and thereafter reducing the pressure so that the matching layer and transducer element retain the desired shape and/or thickness. In this manner, characteristics of thermoplastics are used to form the matching layer into a desired shape and/or thickness, thereby tuning the matching layer to the desired acoustic impedance, and shaping if desired. For example, in one aspect, the matching layer and transducer element have a desired radius of curvature when in the desired shape.

Other features and advantages of the invention will appear from the following description in which the preferred embodiment has been set forth in detail in conjunction with the accompanying drawings.

DESCRIPTION OF THE SPECIFIC EMBODIMENTS

Figure 1A:
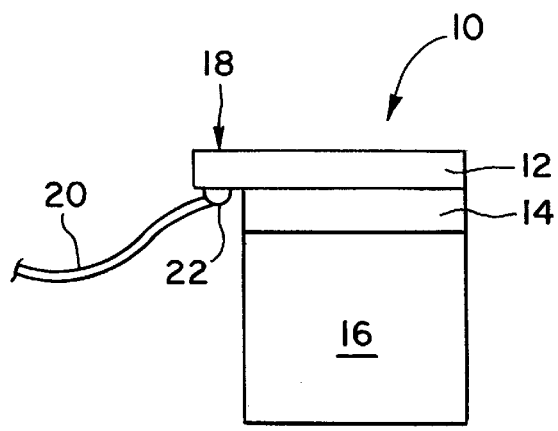
FIGS. 1A and 1B provide a side view and an exploded side view, respectively, of a transducer package for an imaging catheter according to the present invention.
Figure 1B:
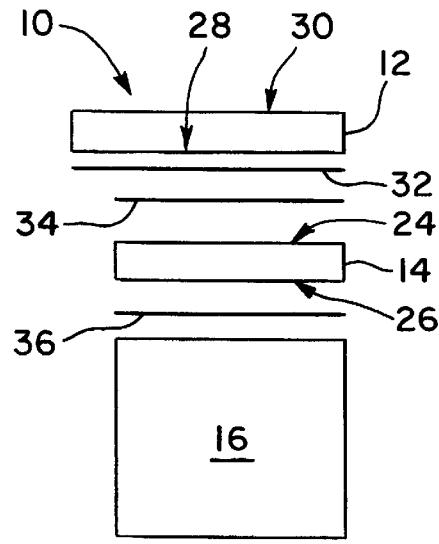

FIGS. 1A and 1B depict an exemplary transducer package 10 according to the present invention. Transducer package 10 includes a transducer element 14, a matching layer 12 and a backing material 16. Matching layer 12 is operably attached to transducer element 14 in a manner in which an overhang portion 18 of matching layer 12 is created. A lead 20 is operably attached to overhang portion 18 using an attachment point 22. In this manner, lead 20 is attached to transducer package 10 in an off-aperture configuration. More specifically, lead 20 is attached by attachment point 22 to overhang portion 18 whereby attachment point 22 does not interfere with ultrasound signals transmitted from and received by transducer element 14.

As shown in FIG. 1B, transducer element 14 has a first surface 24 and a second surface 26. First and second surfaces 24, 26 each preferably include an electrode, such as gold, chrome gold, and the like electrodes, operably attached thereto. In this manner, positive and negative electrode connections can be made to transducer element 14. Transducer element 14 may comprise piezocomposite materials, piezoceramics (such as PZT), piezoplastics, and the like.

Matching layer 12 similarly has a third surface 28 and a fourth surface 30. Matching layer 12 may comprise electrically conductive materials, such as silver filled epoxy, tungsten-filled epoxy, or the like, or electrically non-conductive materials, such as mylar, polyimide, polyurethane, or the like, or combinations thereof. Other materials also may be used including silver and tungsten, silver and glass beads, silver and ceramic, and the like. The conductive material layer 32 is operably attached to or forms a part of matching layer 12. Preferably, conductive material layer 32 comprises gold, chrome-gold, titanium-gold, or the like.

Preferably, matching layer 12 is operably attached to transducer element 14 using a thin layer of adhesive 34. More specifically, conductive material layer 32 is operably attached to first surface 24 by adhesive layer 34. Adhesive layer 34 is thin enough to be generally acoustically transparent. Adhesive layer 34 preferably comprises epoxy, which may be electrically conductive or non-conductive epoxy.

The use of an electrically conductive adhesive layer 34 establishes an electrical connection between transducer element 14 and matching layer 12. More specifically, adhesive layer 34 establishes an electrical connection between the electrode operably attached to first surface 24 of transducer element 14, and conductive material layer 32 operably attached to or comprising a part of third surface 28 of matching layer 12.

Alternatively, matching layer 12 can be operably attached to transducer element 14 using a thin layer of electrically non-conductive adhesive. In such an embodiment, the non-conductive adhesive layer is thin enough to permit a molecular contact between first surface 24 and third surface 28. The result is an ohmic, electrically-conductive contact. In addition, some roughness to third surface 28 and/or to first surface 24 facilitates the electrically conductive bond.

Similarly, second surface 26 of transducer element 14 is operably attached to backing material 16 using an adhesive layer 36. In this manner, transducer package 10 comprises the stacked configuration shown in FIG. 1A.

Backing material 16 is selected to have sound attenuating qualities so that ultrasound signals propagated into the backing are not reflected by backing material 16, which would result in artifacts. Backing material 16 may comprise electrically conductive material, such as epoxy, silver/tungsten epoxy or the like. In such an embodiment, electrically conductive backing material 16 provides a back side electrical connection or negative conductive path or ground to the electrode attached to second surface 26 of transducer element 14.

Alternatively, backing material 16 may comprise electrically non-conductive material, such as epoxy, polyurethane, rubber or the like.

Transducer package 10 eliminates the need to solder or otherwise affix an electrical connection, such as lead 20, directly to transducer element 14 or to the non-overhang portion of matching layer 12. Lead attachment point 22, which may include silver, gold/chrome, gold/chrome/nickel, copper or the like, is made to overhang portion 18. By making attachment point 22 to overhang portion 18, instead of to first surface 24 or to the non-overhang portion of fourth surface 30, attachment point 22 does not interfere with ultrasound signals sent and/or received by transducer element 14. As a result, the variability of attachment point 22 size and location is a reduced concern due to its minimal impact on transducer element 14 performance.

Figure 1C:
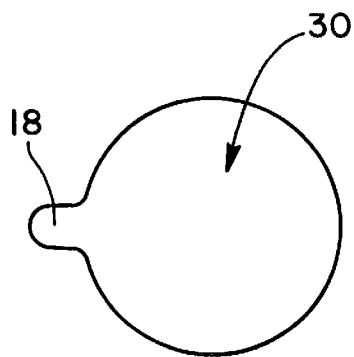
FIGS. 1C–1F are alternative top views of the transducer package depicted in FIGS. 1A and 1B.
Figure 1D:
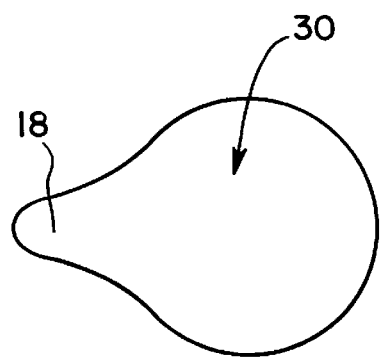
Figure 1E:
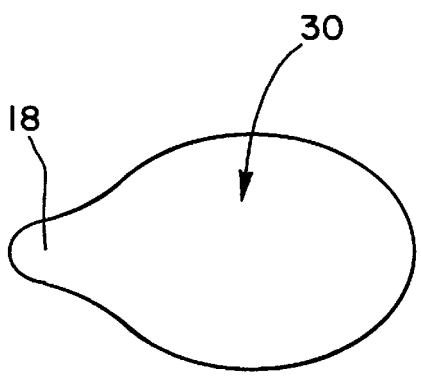
Figure 1F:
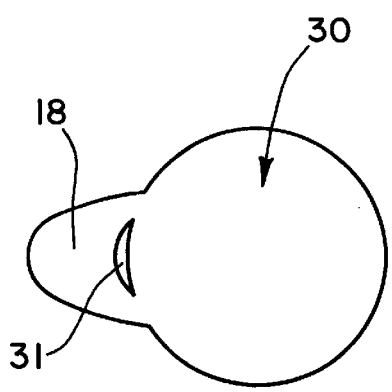

FIG. 1C depicts a top view of transducer package 10. As shown, overhang portion 18 is formed due to third surface 28 having a larger surface area than first surface 24. In this manner, matching layer 12 and transducer element 14 may be operably coupled together in a manner which completely covers first surface 24 and also creates overhang portion 18. FIG. 1C depicts transducer package 10 as having a generally circular cross-section with overhang 18 protruding therefrom. It will be appreciated by those skilled in the art that overhang portion 18 may comprise a variety of shapes depending upon the particular transducer package 10 desired. For example, FIG. 1D depicts a larger overhang portion 18. Similarly, FIG. 1E depicts a generally elliptical fourth surface 30 with overhang portion 18 extending from one edge of the major axis. FIG. 1F depicts an opening 31 through overhang portion 18 to permit flexing of overhang portion 18 when the transducer is affixed to, for example, a housing as part of an imaging catheter (not shown). Such a configuration may be desireable to reduce stresses on the transducer when the housing is rotated. Other shapes for transducer package 10 are anticipated within the scope of the present invention, including oval and rectangular. Transducer packages 10 also may include additional matching layers having the similar shape and size as matching layer 12 depicted in FIG. 1A, or a shape and size similar to the underlying transducer element 14.

Figure 2:
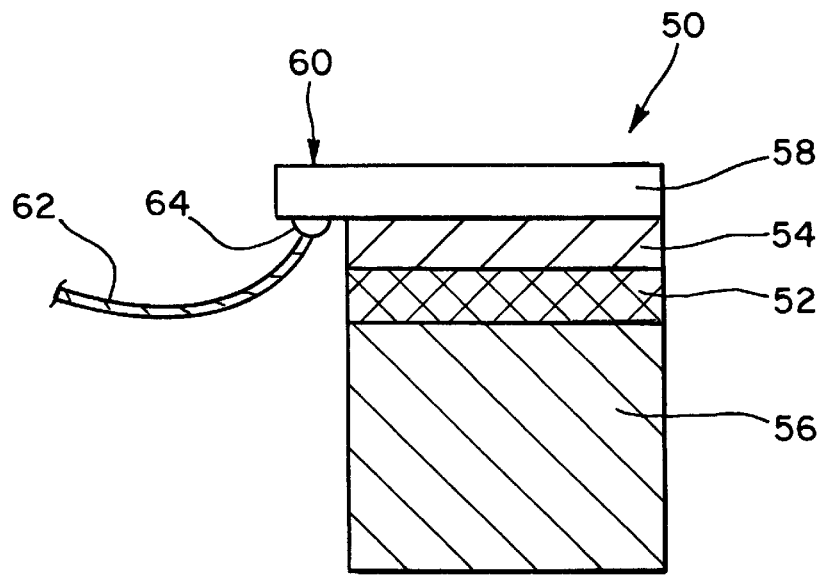
FIG. 2 is a cross-sectional side view of an alternative transducer package according to the present invention.

Turning now to FIG. 2, an alternative embodiment of a transducer package 50 will be described. Transducer package 50 includes a first matching layer 54 operably attached to a transducer element 52 as previously described in conjunction with FIG. 1. Similarly, transducer element 52 is operably attached to a backing material 56 as previously described in conjunction with FIG. 1. Transducer package 50 further includes a second matching layer 58 operably attached to first matching layer 54. Second matching layer 58 defines an overhang portion 60 to which a lead 62 is operably attached using an attachment point 64, as previously described in conjunction with FIG. 1.

Multiple matching layers 54, 58 result in improved efficiency and bandwidth compared to single matching layer designs, due in part to providing smaller, but more frequent impedance changes between the transducer and the surrounding tissue or fluid to be imaged by transducer package 50.

In this particular embodiment, first matching layer 54 comprises a thermoplastic. By having matching layer 54 comprise a thermoplastic, matching layer 54 can be tuned to a desired acoustic impedance as described in greater detail in conjunction with FIG. 4. For example, first matching layer 54 can be conformed under desired pressures and temperatures to have a certain dimension and thickness. First matching layer 54 is shaped so that the acoustic impedance of first matching layer 54 is between the acoustic impedance of transducer element 52 and that of second matching layer 58. First matching layer 54 will necessarily provide a conductive path between transducer element 52 and second matching layer 58, for example, by comprising an electrically conductive material. It will be appreciated by those skilled in the art that matching layer 12 described in conjunction with FIG. 1 also may include a thermoplastic.

Figure 3:
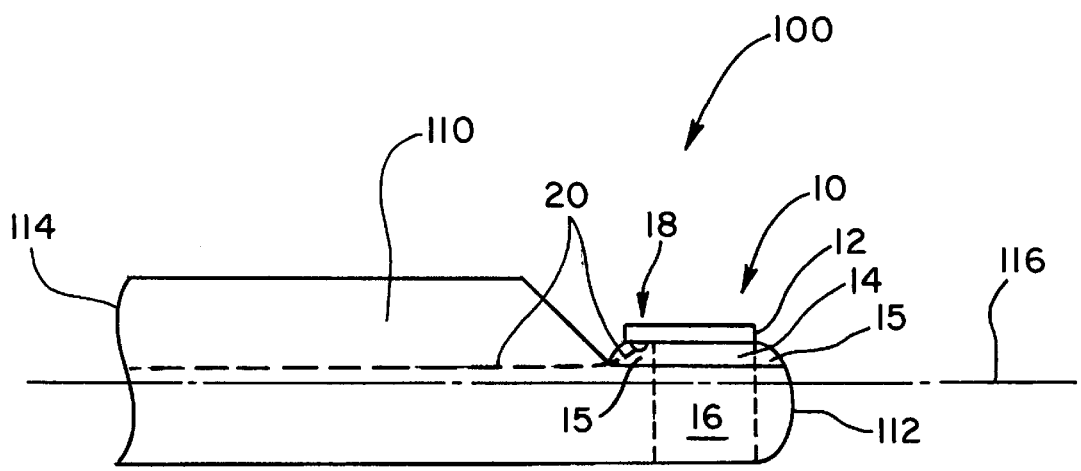
FIG. 3 depicts a side view of an imaging assembly according to the present invention.

Turning now to FIG. 3, an imaging assembly 100 according to the present invention will be described. Imaging assembly 100 includes a housing 110, having a distal end 112, a proximal end 114 and a longitudinal axis 116. While housing 110 is shown to have a generally cylindrical shape, other housing 110 shapes are anticipated within the scope of the present invention.

Housing 110 preferably comprises stainless steel, nickel-plated steel, tin-plated steel, gold-plated steel or the like. Such materials provide sufficient mechanical strength to enable housing 110 to be operably attached to a drive cable, such as a stainless steel drive cable (not shown in FIG. 3). Exemplary drive cables are described in U.S. patent application Ser. No. 09/017,578, entitled "Integrated Coaxial Transmission Line and Flexible Drive Cable", the complete disclosure of which is incorporated herein by reference. Housing 110 also can comprise an epoxy-like material, plastics or the like. Such materials provide desirable sound attenuating and/or electrical conductivity properties.

Imaging assembly 100 further includes a transducer package. While FIG. 3 depicts transducer package 10 as described in conjunction with FIG. 1, imaging assembly 100 alternatively may include transducer package 50 as described in conjunction with FIG. 2. As shown in FIG. 3, lead 20 is operably attached to overhang portion 18 in a manner which does not adversely effect ultrasound signals being transmitted from or received by transducer element 14. A sealant 15 may be used to seal the edges of transducer element 14 to provide protection from, for example, fluids. Sealant 15 may comprise an epoxy, urathane, and the like.

Typically, imaging assembly 100 is disposed within a lumen or sheath (not shown) and is operably attached to a drive cable, such as an integrated coaxial transmission line and drive cable (not shown). This results in a mechanical connection between imaging assembly 100 and the drive cable. Lead 20 preferably is operably attached to the integrated transmission line and drive cable at proximal end 114. The rotation of the drive cable, in turn, rotates imaging assembly 100.

Figure 4:
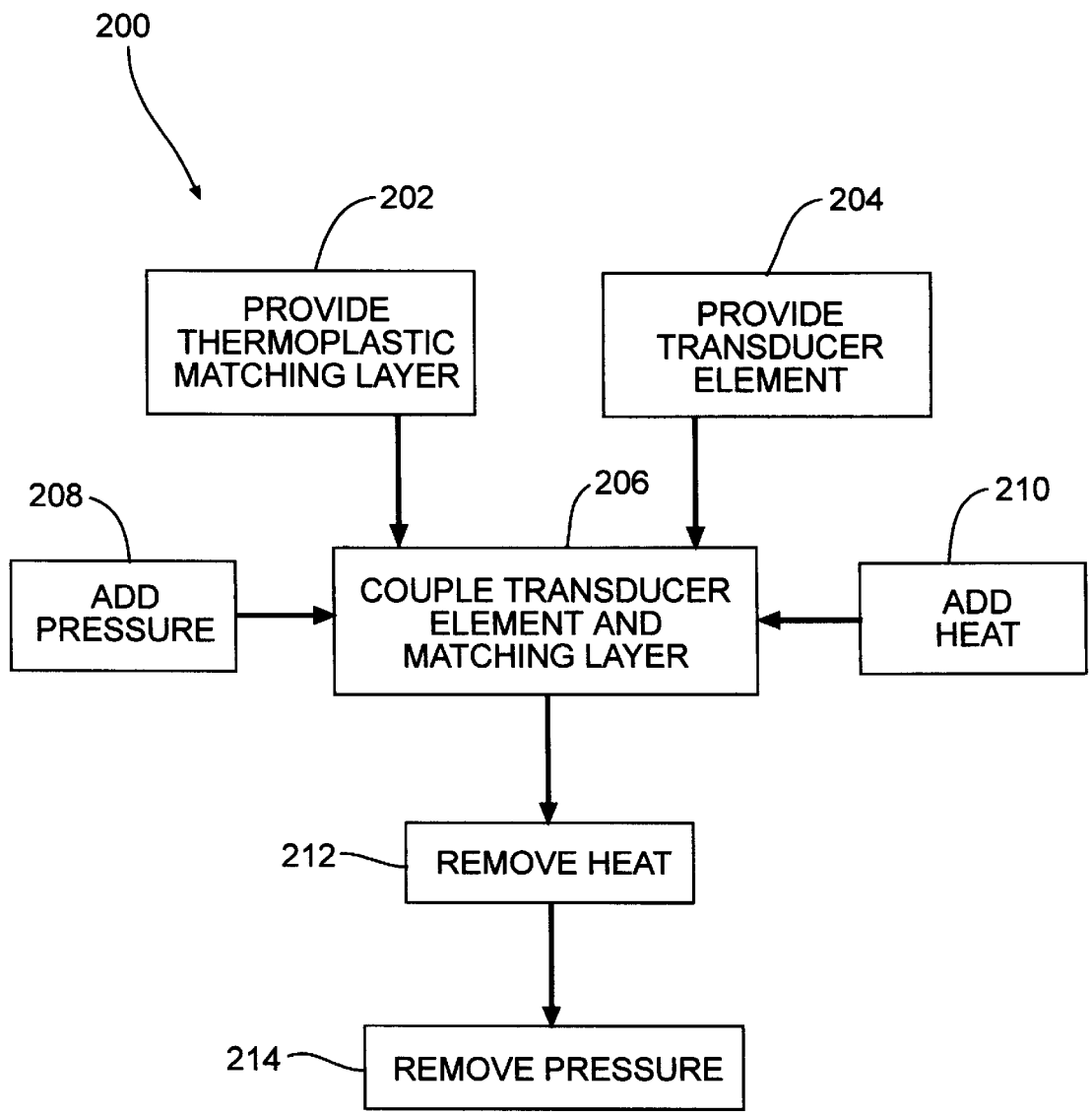
FIG. 4 is a flow chart representing a method of the present invention.

Turning now to FIG. 4, exemplary methods of making transducer packages according to the present invention will be described. FIG. 4 is a schematic of an exemplary method 200 which includes the steps of providing a thermoplastic matching layer 202 and providing a transducer element 204. The transducer element and thermoplastic matching layer are coupled 206 under a desired pressure and temperature range. More specifically, pressure is added 208 and heat is added 210 while the transducer element and matching layer are coupled 206. For example, in one embodiment the coupling step occurs under a pressure in the range from about 5 PSI to about 100 PSI, and a temperature in the range from about 50 degrees Celsius to about 150 degrees Celsius. This process takes advantage of characteristics of thermoplastic whereby under increased pressure and temperature, the thermoplastic takes on a desired shape and/or thickness. The method includes removing the heat 212 from the coupled transducer element/matching layer while maintaining the pressure. This permits the thermoplastic matching layer to retain the desired shape. Once the thermoplastic matching layer has set, the pressure is removed 214. By controlling the thickness and shape of the matching layer, the acoustic impedance can be tuned to a desired level.

Figure 5A:
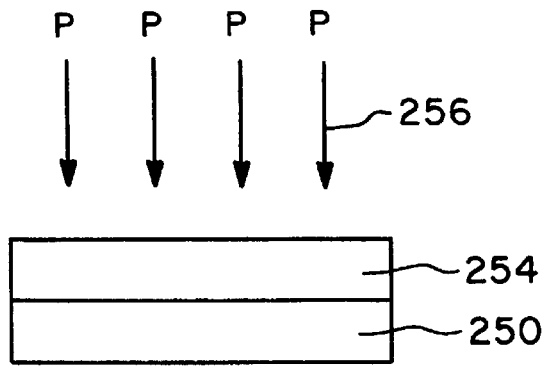
FIGS. 5A–5C depict side views of alternative transducer element/matching layer pairs for use in transducer packages and imaging assemblies of the present invention.

FIG. 5A shows a thermoplastic matching layer 254 operably attached to a transducer element 250 as described in conjunction with FIGS. 1 and 2. A desired pressure 256 is applied to matching layer 254 and transducer element 250 as shown in FIG. 4. As shown in FIG. 5A, pressure 256 may be uniformly applied so that the matching layer and transducer element have surfaces that are generally flat.

Figure 5B:
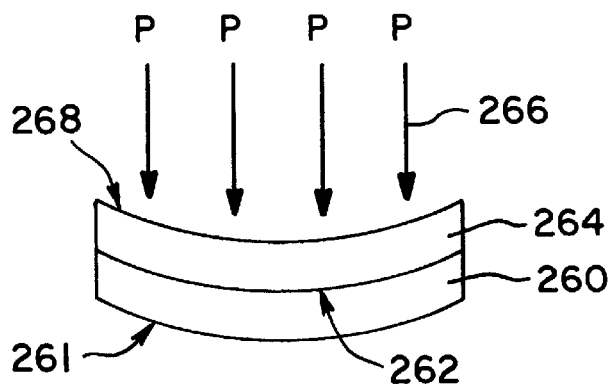
Figure 5C:
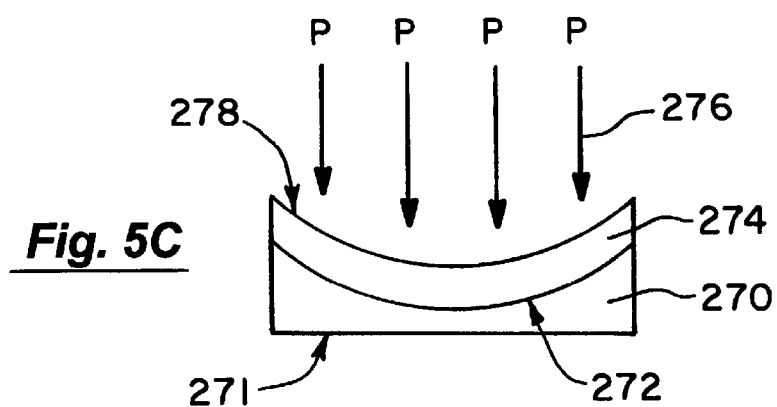

Alternatively, in some instances it is preferable to have a focused transducer element such as that shown in FIGS. 5B–5C. In this manner, by varying the pressure (shown by arrows 266) along a surface 268 of a matching layer 264, a curved matching layer and transducer package can be formed. For example, the embodiment depicted in FIG. 5B represents a true focus transducer 260 in that the thickness of transducer element 260 remains generally constant throughout transducer element 260. In other words, a first transducer surface 262 is separated from a second transducer surface 261 by a generally uniform distance. Similarly, matching layer 264 is used with a generally uniform thickness. Alternatively, matching layer 264 may have a variable thickness which in effect produces a generally flat surface 268 (not shown).

As shown in FIG. 5C, the use of a thermoplastic matching layer 274 also may be used with a tapered focus transducer element 272. In this configuration, the thickness of transducer element 270 varies. In other words, a first transducer surface 272 is not a uniform distance from a second transducer surface 271. Pressure, as indicated by arrows 276, can be used to form matching layer 274 having a curved surface 278 to transducer element 270. Alternatively, matching layer 274 can be operably attached to transducer element 272 and have a generally flat surface 278 (not shown).

Figure 6A:
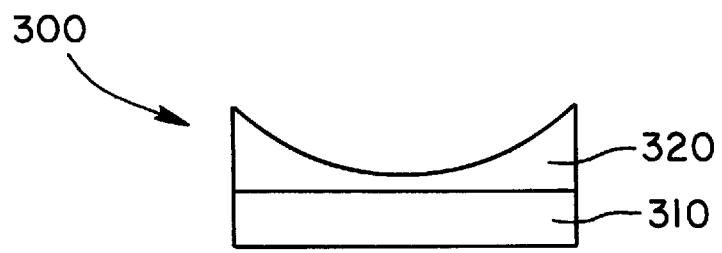
FIGS. 6A–6D depict side views of additional transducer element/matching layer pairs for use in transducer packages and imaging assemblies of the present invention.
Figure 6B:
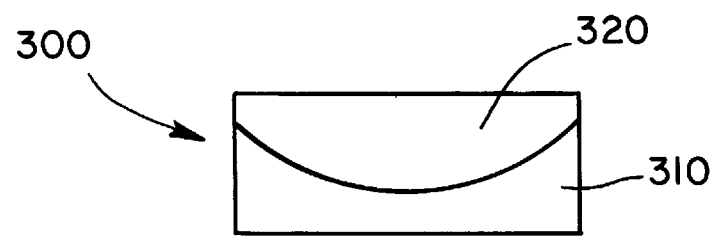

FIGS. 6A–6D depict a transducer/matching layer combination 300 having a variety of shapes. Each combination 300 has a transducer element 310 operably attached to a matching layer 320. It will be appreciated by those skilled in the art that backing layers and additional matching layers (not shown) also may be used with combinations 300. FIG. 6A depicts transducer element 310 having a generally uniform thickness throughout. Transducer element 310 is coupled to matching layer 320 having a varying thickness, with matching layer 320 having its greatest thickness near the edges or periphery of combination 300. Combination 300 in FIG. 6B depicts transducer element 310 with varying thickness coupled to matching layer 320 with varying thickness. Transducer 310 has its greatest thickness near the edges thereof, and matching layer 320 has its greatest thickness near the center of combination 300. As a result, combination 300 has a generally flat upper surface.

Figure 6C:
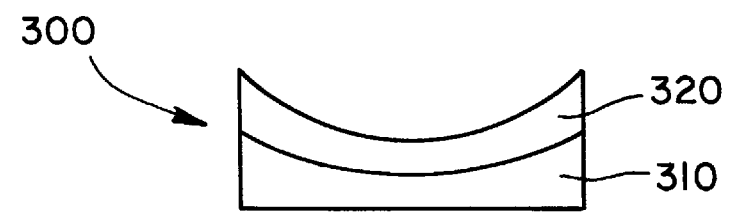
Figure 6D:
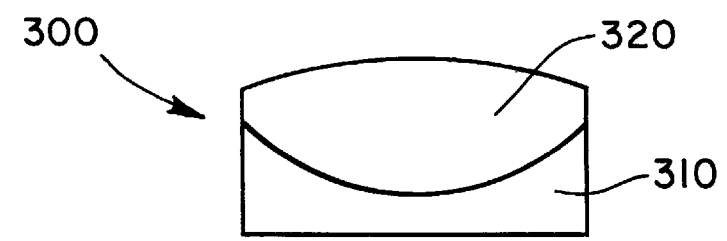

FIG. 6C depicts both transducer element 310 and matching layer 320 having varying thicknesses with each having its greatest thickness near the edges thereof. Finally, FIG. 6D depicts a varying thickness transducer 310 coupled to a varying thickness matching layer 320, where matching layer 320 has a convex upper surface. It will be appreciated by those skilled in the art that FIGS. 6A–6D depict several of a wide range of matching layer/transducer combinations 300 that may be used within the scope of the present invention.

The invention has now been described in detail. However, it will be appreciated that certain changes and modifications may be made. For example, transducer packages 10, 50 may comprise more than one or two matching layers. Therefore, the scope and content of this invention are not limited by the foregoing description. Rather, the scope and content are to be defined by the following claims.

What is claimed is:

1. A transducer package for an imaging catheter comprising:
    at least one transducer element, comprising first and second spaced apart surfaces defining a transducer peripheral edge;
    a matching layer operably attached to said at least one transducer element first surface but not to said peripheral edge to create an overhang portion of said matching layer with respect to each of said at least one transducer element; and
    a lead operably attached to said overhang portion but not to said peripheral edge.

2. A transducer package as in claim 1, wherein:

said transducer element first surface having a first area;

said matching layer comprises third and fourth spaced apart surfaces, said third surface having a second area and being operably attached to said first surface; and wherein said second area is larger than said first area.

3. A transducer package as in claim 2, wherein said matching layer is operably attached to said transducer element so that said third surface completely covers said first surface and produces said overhang portion.

4. A transducer package as in claim 2, wherein said matching layer and said transducer element further comprise a conductive material, so that operably attaching said third surface to said first surface produces an electrically conductive path therebetween.

5. A transducer package as in claim 1, wherein said transducer element is operably attached to said matching layer using an epoxy layer.

6. A transducer package as in claim 1, wherein said matching layer comprises a thermoplastic.

7. The transducer package as in claim 6 wherein said thermoplastic provides a tunable acoustic impedance of said matching layer.

8. A transducer package as in claim 1, wherein said matching layer comprises an uncatalyzed epoxy.

9. A transducer package as in claim 1, further comprising a second matching layer operably attached to said first matching layer.

10. A transducer package as in claim 9, wherein said second matching layer has a different acoustic impedance than said first matching layer.

11. A transducer package as in claim 1, further comprising a backing material operably attached to said transducer element.

12. A transducer package as in claim 1, wherein said transducer element comprises a material selected from a group of materials consisting of piezoceramics, piezocomposites, and piezoplastics.

13. A transducer package as in claim 1, wherein said at least one transducer element has a first curved surface and said matching layer has a second curved surface, said at least one transducer element and said matching layer being operably attached so that said first curved surface is coupled to said second curved surface.

14. The transducer package as in claim 1 wherein said matching layer overhang portion further comprises an internal opening therethrough to facilitate flexing of said overhang portion.

15. An imaging assembly comprising:

a housing having a distal end, a proximal end, and a longitudinal axis; and a transducer package operably attached to said distal end, said transducer package comprising;

at least one transducer element comprising a first surface and a peripheral edge;

a matching layer operably attached to said at least one transducer element to create an overhang portion of said matching layer with respect to each of said at least one transducer element; and a lead operably attached to said overhang portion but not attached to said peripheral edge.

16. An imaging assembly as in claim 15 further comprising a drive cable operably attached to said proximal end.

17. An imaging assembly as in claim 15, wherein said matching layer comprises a thermoplastic.

18. An imaging assembly as in claim 15 wherein said thermoplastic provides a tunable acoustic impedance of said matching layer.

19. A method of making an ultrasound transducer package, comprising:

providing at least one transducer element having first and second electrodes operably attached to first and second transducer element surfaces, respectively, said first and second transducer element surfaces being spaced apart to define a transducer element periphery;

providing a matching layer having at least one electrically conductive surface;

coupling said at least one transducer element to said matching layer conductive surface with an adhesive layer to produce an electrically conductive path between said first electrode and said matching layer conductive surface;

wherein said coupling step creates an overhang portion of said matching layer with respect to each of said at least one transducer element; and attaching a lead to said overhang portion but not to said periphery.

20. A method as in claim 19, wherein said adhesive layer comprises an electrically non-conductive epoxy layer.

21. A method as in claim 19, wherein said matching layer comprises a thermoplastic.

22. A method as in claim 21, wherein said coupling step comprises:

compressing said matching layer and said transducer element together using a desired pressure and a desired temperature;

reducing said temperature after said matching layer and transducer element have been compressed into a desired shape; and reducing said pressure after said reducing said temperature step so that said matching layer and said transducer element retain said desired shape.

23. A method as in claim 22, wherein said matching layer and said transducer element have a desired radius of curvature when in said desired shape.

24. A method as in claim 21 wherein said thermoplastic provides a tunable acoustic impedance of said matching layer.

25. The imaging assembly as in claim 15 wherein said transducer package defines an electrically conductive path from said lead, to said overhang portion and to said first surface exclusive of said periphery.

26. A transducer package as in claim 15 wherein said matching layer overhang portion further comprises an internal opening therethrough to facilitate flexing of said overhang portion.

* * * * *

UNITED STATES PATENT AND TRADEMARK OFFICE
CERTIFICATE OF CORRECTION

PATENT NO. : 6,406,433 B1
DATED : June 18, 2002
INVENTOR(S) : Don S. Mamayek

It is certified that error appears in the above-identified patent and that said Letters Patent is hereby corrected as shown below:

Column 10,
Line 7, please delete "claim 15" and insert -- claim 17 -- therefor.

Signed and Sealed this

Fifth Day of November, 2002

Attest:

JAMES E. ROGAN
Attesting Officer  Director of the United States Patent and Trademark Office